US012607583B2

(12) United States Patent
Yao et al.

(10) Patent No.: US 12,607,583 B2
(45) Date of Patent: Apr. 21, 2026

(54) METHOD FOR ESTABLISHING MATHEMATICAL MODEL OF RELATIONSHIP BETWEEN SPONTANEOUS IMBIBITION VOLUME AND TIME OF POROUS MEDIUM

(71) Applicant: CHINA UNIVERSITY OF GEOSCIENCES (BEIJING), Beijing (CN)

(72) Inventors: Yanbin Yao, Beijing (CN); Zishuo Li, Beijing (CN); Dameng Liu, Beijing (CN); Xiaoxiao Sun, Beijing (CN); Yong Liu, Beijing (CN)

(73) Assignee: CHINA UNIVERSITY OF GEOSCIENCES (BEIJING), Beijing (CN)

( * ) Notice: Subject to any disclaimer, the term of this patent is extended or adjusted under 35 U.S.C. 154(b) by 1078 days.

(21) Appl. No.: 17/691,148

(22) Filed: Mar. 10, 2022

(65) Prior Publication Data

US 2022/0291157 A1     Sep. 15, 2022

(30) Foreign Application Priority Data

Mar. 11, 2021     (CN) .......................... 202110265631.6

(51) Int. Cl.
*G01N 24/08*          (2006.01)
*G01N 1/34*           (2006.01)
(Continued)

(52) U.S. Cl.
CPC ............. *G01N 24/081* (2013.01); *G01N 1/34* (2013.01); *G01N 1/4077* (2013.01); *G01N 33/24* (2013.01);
(Continued)

(58) Field of Classification Search
CPC ...... G01N 24/081; G01N 1/34; G01N 1/4077; G01N 33/24; G01N 2001/4083;
(Continued)

(56) References Cited

U.S. PATENT DOCUMENTS 11,921,069 B1 *   3/2024   Vinegar .................. E21B 7/046
2022/0291411 A1 *   9/2022   Althaus .................... G01V 3/32

FOREIGN PATENT DOCUMENTS

CN          108469406        *   8/2018   ......... G01N 15/0826

OTHER PUBLICATIONS

Lu et al. "Improved Method for Measuring the Permeability of Nanoporous Material and Its Application to Shale Matrix with Ultra-Low Permeability" Materials 2019, 12, 1567; doi: 10.3390/ma12091567 [retrieved on Sep. 4, 2025] (Year: 2019).*
(Continued)

*Primary Examiner* — Emerson C Puente
*Assistant Examiner* — Alfred H B Wechselberger

(57)          ABSTRACT

A method for establishing mathematical model of relationship between spontaneous imbibition volume and time of porous medium includes sample pretreatment, fully-saturation and centrifugal experiments and NMR $T_2$ measurement. First, two rock core samples of predetermined size are selected for cleaning and drying. The first rock sample is vacuumed and injected with water to obtain a saturated sample for NMR $T_2$ measurement. Then, spontaneous imbibition experiment is conducted on another sample, and $T_2$ measurements are conducted to obtain the water distribution and migration characteristics during the imbibition process. Next, the calculation of the imbibition permeability, average capillary pressure and surface relaxivity are conducted based on the NMR data obtained from two samples. Finally,
(Continued)

substitute these parameters into the Handy relationship to obtain a new NMR-based mathematical spontaneous imbibition model.

7 Claims, 3 Drawing Sheets

(51) Int. Cl.

| | | |
|---|---|---|
| *G01N 1/40* | (2006.01) | |
| *G01N 33/24* | (2006.01) | |
| *G06F 30/20* | (2020.01) | |
| *G06F 111/10* | (2020.01) | |

(52) U.S. Cl.
CPC ..... *G06F 30/20* (2020.01); *G01N 2001/4083* (2013.01); *G06F 2111/10* (2020.01)

(58) Field of Classification Search
CPC ......... G01N 2015/0846; G01N 15/082; G01N 33/241; G01N 15/088; G06F 30/20; G06F 30/25; G06F 30/27; G06F 30/28; G06F 2111/00–2119/22; G01R 33/448
See application file for complete search history.

(56) References Cited

OTHER PUBLICATIONS

Kuzyk, M. "Relationship Between the Molecular and Bulk Response" Chapter 3 in Characterization Techniques and Tabulations for Organic Nonlinear Optical Materials, 1st Edition (Year: 1998).*
Vevle, J. "NMR measurements of wettability alternation in Berea Sandstone" [Thesis] Petroleum Technology—Reservoir Physics, Centre for Integrated Petroleum Research, Department of Physics and Technology, University of Bergen (Year: 2011).*

* cited by examiner

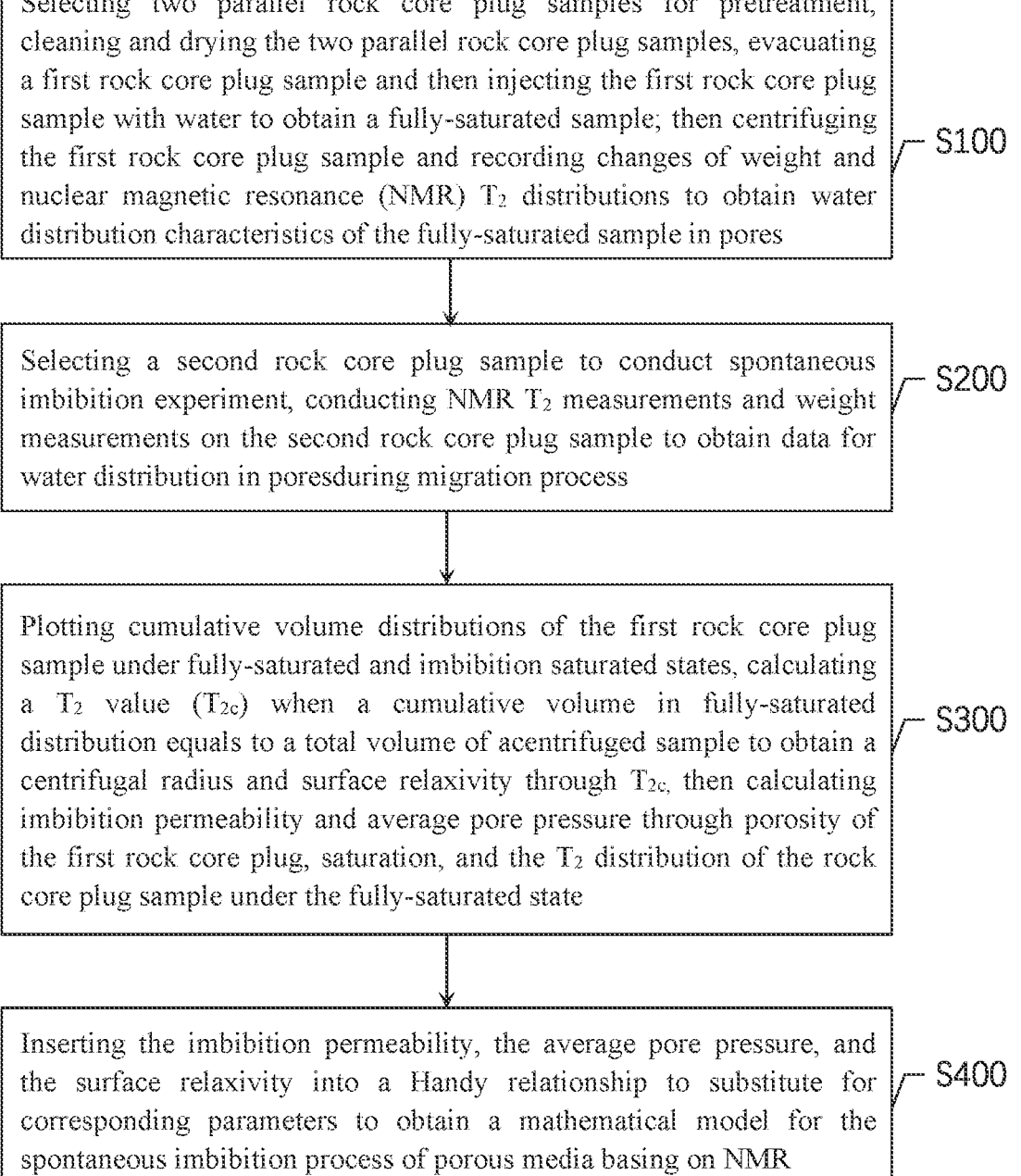

Selecting two parallel rock core plug samples for pretreatment, cleaning and drying the two parallel rock core plug samples, evacuating a first rock core plug sample and then injecting the first rock core plug sample with water to obtain a fully-saturated sample; then centrifuging the first rock core plug sample and recording changes of weight and nuclear magnetic resonance (NMR) $T_2$ distributions to obtain water distribution characteristics of the fully-saturated sample in pores ⌐ S100

Selecting a second rock core plug sample to conduct spontaneous imbibition experiment, conducting NMR $T_2$ measurements and weight measurements on the second rock core plug sample to obtain data for water distribution in poresduring migration process ⌐ S200

Plotting cumulative volume distributions of the first rock core plug sample under fully-saturated and imbibition saturated states, calculating a $T_2$ value ($T_{2c}$) when a cumulative volume in fully-saturated distribution equals to a total volume of acentrifuged sample to obtain a centrifugal radius and surface relaxivity through $T_{2c}$, then calculating imbibition permeability and average pore pressure through porosity of the first rock core plug, saturation, and the $T_2$ distribution of the rock core plug sample under the fully-saturated state ⌐ S300

Inserting the imbibition permeability, the average pore pressure, and the surface relaxivity into a Handy relationship to substitute for corresponding parameters to obtain a mathematical model for the spontaneous imbibition process of porous media basing on NMR ⌐ S400

FIG. 1

METHOD FOR ESTABLISHING MATHEMATICAL MODEL OF RELATIONSHIP BETWEEN SPONTANEOUS IMBIBITION VOLUME AND TIME OF POROUS MEDIUM

TECHNICAL FIELD

The present disclosure generally relates to the reservoir evaluation in geology field and, in particular to a method for establishing mathematical model of relationship between spontaneous imbibition volume and time of porous medium on existing technologies.

BACKGROUND

Spontaneous imbibition is a natural phenomenon that the wetting phase fluid flows into the pores in porous media driven by capillary force. It has a broad research space in material science, biology and geology. In petroleum engineering, spontaneous imbibition has a complex impact on the recovery of oil and gas during reservoir development because it not only participates in the production of oil and gas, but also leads to the retention of fracturing fluid. Therefore, the evaluation of the spontaneous imbibition characteristics in tight reservoirs is of great significance to solve the problems related to hydraulic fracturing.

At present, spontaneous imbibition experiment has become a popular method to study the imbibition characteristics of porous media. Many researchers have found that the imbibition velocity is closely related to the porosity, permeability, pore shape, and fluid properties. Previous studies have integrated various parameters, such as the roundness and tortuosity of pores, the gravity of wetting phase fluids and the pore fractal dimension into their derivation process to obtain a more comprehensive imbibition model. However, most of these studies are highly dependent on the traditional methods to calculate the porosity, permeability and mineral composition data, which is difficult to directly reflect the fluid distribution and migration characteristics during imbibition process in different types of porous media. Besides, for porous media with low to ultra-low pore permeability like shales, the accuracy of physical parameters obtained by conventional experimental methods is not high. Thus, the imbibition behavior of tight reservoirs is still poorly understood.

In recent years, nuclear magnetic resonance spectroscopy (NMR) have been widely used to characterize the porosity, permeability and fluid transport in porous media, and the pore size distribution analysis based on NMR $T_2$ spectra has become a popular method to study imbibition behavior in porous media. The $T_2$ data interpreted by NMR principles can reflect the characteristics of fluids during transport and migration process, and thus the parameters related to spontaneous imbibition can be obtained directly or indirectly to establish the imbibition model.

Considering the good applicability of the Handy relationship to conventional porous media, lots of existing imbibition models are derived based on it. But for complex porous media, especially in tight reservoirs like shales, the definition of capillary pressure and permeability in the Handy relationship is unclear and hard to obtain, which affects the evaluation of imbibition process during fracturing process. Thus, a comprehensive imbibition model is in great need in the further.

SUMMARY

The present disclosure provides method for establishing mathematical model of relationship between spontaneous imbibition volume and time of porous medium1 based on modifications on a classical Handy relationship.

Specifically, the following is steps to derive a spontaneous imbibition model using rock core plug samples samples.

Step 100, selecting two parallel rock core plug samples for pretreatment, cleaning and drying the two parallel rock core plug samples, evacuating a first rock core plug sample and then injecting the first rock core plug sample with water to obtain a fully-saturated sample; then centrifuging the first rock core plug sample and recording changes of weight and nuclear magnetic resonance (NMR) $T_2$ distributions to obtain water distribution characteristics of the fully-saturated sample in pores.

Step 200, selecting a second rock core plug sample to conduct spontaneous imbibition experiment, conducting NMR $T_2$ measurements and weight measurements on the second rock core plug sample to obtain data for water distribution in pores during migration process.

Step 300, plotting cumulative volume distributions of the first rock core plug sample under fully-saturated and imbibition saturated states, calculating a $T_2$ value ($T_{2c}$) when a cumulative volume in fully-saturated distribution equals to a total volume of a centrifuged sample to obtain a centrifugal radius and surface relaxivity through $T_{2c}$, then calculating imbibition permeability and average pore pressure through porosity of the first rock core plug, saturation, and the $T_2$ distribution of the rock core plug sample under the fully-saturated state.

Step 400, inserting the imbibition permeability, the average pore pressure, and the surface relaxivity into a Handy relationship to substitute for corresponding parameters to obtain a mathematical model for the spontaneous imbibition process of porous media basing on NMR.

The present disclosure overcomes the limitations of the calculation method of permeability and capillary pressure in the existing imbibition models based on handy relationship for complex porous media like shale, and provides a new method for the imbibition evaluation in tight reservoirs.

The model proposed in the present disclosure can be applied to simulate the relationship of imbibition volume versus time in porous media, which has broad prospects in petroleum engineering, especially for the evaluation of fracturing fluid migration during hydraulic fracturing in tight reservoirs. Besides, this model can also be applied to study the imbibition behavior of carbonate, sandstone and soil. Besides, it also has wide application prospect in the evaluation of the physical property of man-made materials.

BRIEF DESCRIPTION OF THE DRAWINGS

FIG. 1 is a flowchart of preliminarily obtaining a mathematical model according to one embodiment of the present disclosure.

DETAILED DESCRIPTION

Figure 2:
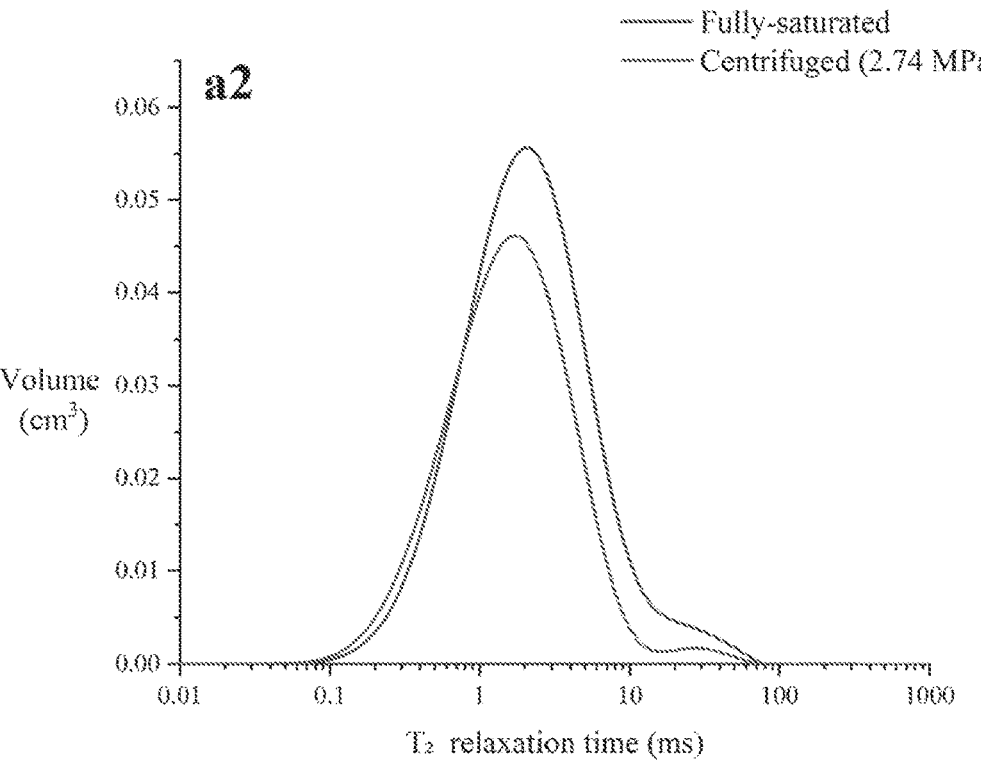
FIG. 2 is a schematic diagram of NMR $T_2$ distributions of a2 under saturated and centrifuged states according to one embodiment of the present disclosure.

A specific structure and implementation process of the present disclosure are described in detail below with reference to specific embodiments and drawings.

Among existing technologies, a classical Handy relationship is generally selected to derive the mathematical co-current imbibition model to simulate the relationship between imbibition volume and time:

$$M = A\sqrt{\frac{2K\varphi S_w P}{\mu}t}; \qquad (1)$$

where M is the volume of imbibed wetting phase fluid (cm$^3$), A is the contact area between wetting phase and porous media (cm$^2$), $\varphi$ is the porosity, $S_w$ is the wetting phase saturation in porous media, $\mu$ is the viscosity of wetting phase (Pa·s), t is the imbibition time (s), and K is the permeability of wetting phase (mD).

Since the Handy relationship lack applicability to the tight reservoirs, the present disclosure uses the imbibition permeability $K_{imb}$ and average capillary pressure $P_{ave}$ to substitute for permeability and capillary pressure in conventional imbibition models. In this way, the limitations of the Handy relationship can be solved because the acquisition of permeability and capillary pressure for tight reservoirs will no longer rely on the conventional means which is not suitable for complex porous media. Besides, the calculation methods of new parameters in the present disclosure also provide a new way for spontaneous imbibition evaluation of hydraulic fracturing process of tight reservoirs such as shale.

As shown in FIG. 1, in one embodiment of the present disclosure, a method to establish a mathematical model to evaluate the imbibition volume verses time is disclosed, which comprises the following steps:

Step 100, selecting two parallel rock core plug samples for pretreatment, cleaning and drying the two parallel rock core plug samples, evacuating a first rock core plug sample and then injecting the first rock core plug sample with water to obtain a fully-saturated sample; then centrifuging the first rock core plug sample and recording changes of weight and nuclear magnetic resonance (NMR) T$_2$ distributions to obtain water distribution characteristics of the fully-saturated sample in pores.

Before experiment, the original core samples need to be calibrated to obtain their NMR base signal. First, the core samples are cleaned and dried until the mass remained unchanged, and then the transverse relaxation time measurement is conducted on each sample to obtain the base signal. The base signals of samples are deducted in the following NAR measurements.

In the present disclosure, the CPMG pulse sequence is applied in NMR measurements, and parameters for all NMR T$_2$ measurements are set as follows: echo spacing of 0.132 ms, echo numbers of 3788, scan number of 32, and recycle delay of 750 ms.

The selection, preparation and cleaning of rock samples are conducted according to the national standard of GB/T 29172-2012 "Practices for core analysis". Two parallel core plug samples with 2.5 cm in diameter and 5 cm in height are drilled from the rock vertical to its bedding direction. They are cleaned and dried at 105° C. for 48 hours until mass remained unchanged to remove the residual water. Then, the mass of dry samples m0 are measured using a high precise electronic balance, and their helium porosity $\varphi$ and contact angle $\theta$ are then measured according to the national standard.

The processes of the saturation and centrifugal experiments for the first core sample are: put the first core sample into a vacuum pump and vacuum for 8 h, then inject 3% (about 30000 ppm) KCl solution into the pump and pressurize to 30 MPa (about 3000 psi). Maintain the pressure for 24 hours to ensure the core sample reaches fully-saturated state. The KCl solution used in this step can avoid the swelling of clay in core sample.

After fully-saturated process, the first sample is taken out from pump and the excess liquid is wiped off from surface, then it is weighed and the mass is recorded as m1. After that, the NMR analysis is conducted to obtain the T$_2$ distribution of pores and the mass of water m (m=m$_1$−m$_0$) for the saturated sample.

The saturated sample is then centrifuged under centrifugal pressure P$_C$, and the mass of sample before and after centrifugation is recorded. NMR measurements are also conducted during this process to obtain the T$_2$ distributions of fully-saturated and centrifugated sample to provide calculation basis for subsequent calculation.

Step 200, selecting a second rock core plug sample to conduct spontaneous imbibition experiment, conducting NMR T$_2$ measurements and weight measurements on the second rock core plug sample to obtain data for water distribution in pores during migration process.

Step 300, plotting cumulative volume distributions of the first rock core plug sample under fully-saturated and imbibition saturated states, calculating a T$_2$ value (T$_{2c}$) when a cumulative volume in fully-saturated distribution equals to a total volume of a centrifuged sample to obtain a centrifugal radius and surface relaxivity through T$_{2c}$, then calculating imbibition permeability and average pore pressure through porosity of the first rock core plug, saturation, and the T$_2$ distribution of the rock core plug sample under the fully-saturated state.

To derive the mathematical model for the relationship of imbibition volume versus time, this step needs to calculate the imbibition permeability $K_{imb}$ and the average pore pressure $P_{ave}$ first, and the surface relaxivity $\rho_2$ is necessary to calculate the imbibition permeability $K_{imb}$.

T$_2$ distribution of the porous media after imbibition can directly reflect the relationship of the volume of fluid in pores and its corresponding transverse relaxation time, which is the distribution of pore volume $V_{imb(T2)}$ to T$_2$ value from $T_{2max}$ to $T_{2min}$. If the porosity and water saturation are known, the imbibition permeability of porous medium can be obtained using the T$_2$ distribution of the second rock core sample at the end of spontaneous imbibition experiment.

The surface relaxivity of porous media $\rho_2$ is a constant closely related to its properties, and in the present disclosure the centrifugal method is selected for its calculation. After NMR measurements on the first sample, the T$_2$ distribution data of fully-saturated and centrifuged states can be obtained. Due to the fluid in pores larger than centrifugal radius can be completely removed from the sample, when the first sample's cumulative amplitude of T$_2$ distribution of fully-saturated state from $T_{2min}$ to $T_{2max}$ equals its total amplitude of T$_2$ distribution in centrifuged state, this T$_2$ value is the $T_{2cutoff}$ (or $T_{2c}$) corresponding to centrifugal radius r$_c$ for rock sample.

The relationship between centrifugal pressure $P_c$ and centrifugal radius $r_c$ is:

$$r_c = \frac{2\sigma}{P_c}. \qquad (2)$$

Besides, according to the principle of NMR, during the measurement, $T_2$ distribution is affected by three possible relaxation mechanisms: bulk relaxation, surface relaxation and diffusion relaxation. Since most of the fluid in porous media is under capillary bound state and magnetic field can be neglected in this experiment, the resulting NMR measurement can be mainly attributed to surface relaxation $T_{2s}$.

$$\frac{1}{T_2} \approx \frac{1}{T_{2S}} = \rho_2 \left( \frac{S_{pore(r)}}{V_{pore(r)}} \right) \qquad (3)$$

where $\rho_2$ is the surface relaxivity (nm/ms), constant; $S_{pore(r)}$ and $V_{pore(r)}$ are the surface area and volume of pores with radius r in porous medium. It can be seen from the relationships above that $T_2$ is direct proportion to r, and $T_2$ can be used to evaluate the pore size.

Therefore, $\rho_2$ can be calculated by inserting $r_c$, $T_{2c}$ into relationship (3):

$$\rho_2 = \frac{r_c}{F_s T_{2c}}; \qquad (4)$$

where Fs is the pore shape factor which is equal to 2 for a cylindrical pore and 3 for a spherical pore.

Based on the understandings above, we can further derive the calculation method for imbibition permeability $K_{imb}$:

The Kozeny Carman relationship is a semi empirical relationship frequently used to study the percolation ability of porous media:

$$K = \frac{\varphi^3}{C\gamma^2}; \qquad (5)$$

where $\varphi$ is the porosity; C is the Kozeny-Carman constant, which is closely related to pore shape and is equal to 6 for capillaries; $\gamma$ is the ratio of total surface area of pores to the sample volume ($V_{sample}$), which is:

$$\gamma = \frac{S}{V_{sample}}; \qquad (6)$$

where S is the total surface area of pores (m$^2$); $V_{sample}$ is the sample volume (m$^3$).

The derivation of Kozeny-Carman relationship adopted the hypothesis that all pores on flow direction can participate in the imbibition process. However, researchers found that only some portion of the pores can participate during the imbibition process, which means although some sealed pores contribute to the total porosity, they do not participate in the imbibition. Therefore, the parameters in the Kozeny-Carman relationship should be different for the imbibition process.

In this embodiment, the porosity, volume and surface area of pores participated in imbibition in porous medium (called imbibition pores) is recorded as $\varphi_{imb}$, $V_{imb}$ and $S_{imb}$ respectively. Thus, $V_{imb}$ and $\varphi_{imb}$ have the following relationship with total porosity $\varphi$ and saturation $S_w$:

$$\varphi_{imb} = \frac{V_{imb}}{V_{sample}} = \frac{VS_w}{V_{sample}} = \varphi S_w; \qquad (7)$$

where V is the total pore volume (cm$^3$) which can be obtained by the mass difference of fully-saturated and dry sample.

The imbibition permeability $K_{imb}$ for imbibition process can be obtained by inserting $\varphi_{imb}$, $V_{imb}$ and $S_{imb}$ into the Kozeny-Carman relationship:

$$K_{imb} = \frac{\varphi_{img}^3}{C\gamma^2} = \frac{\varphi_{imb}^3 V_{sample}^2}{CS_{imb}^2} = \frac{\varphi^3 S_w^3 V_{sample}^2}{CS_{imb}^2}. \qquad (8)$$

During the spontaneous imbibition process, the surface area of imbibition pores $S_{imb}$ is the sum of the surface area of pores participated in imbibition process, and the volume of sample $V_{sample}$ equals the ratio of total pore volume and porosity, thus:

$$S_{imb} = \sum_{r=r_{min}}^{r_{max}} S_{imb}(r); \text{ and} \qquad (9)$$

$$V_{sample} = \frac{V}{\varphi}; \qquad (10)$$

where $r_{max}$ is the maximum pore radius and $r_{min}$ is the minimum pore radius in porous medium; $S_{imb(r)}$ is the pore surface area of the imbibition pores with radius r. The summation form in relationship (9) means the sum of the surface area of the smallest to largest imbibition pores in porous medium. Inserting Eqs. (9) and (10) into relationship (8) to obtain:

$$K_{imb} = \frac{\varphi S_w^2 V^2}{C\left(\sum\limits_{r=r_{min}}^{r_{max}} S_{imb}(r)\right)^2}. \qquad (11)$$

Relationship (11) is the relationship to calculate imbibition permeability.

Meanwhile, relationship (3) can be rewritten as:

$$S_{pore(r)} = \frac{V_{pore(r)}}{\rho_2 T_2}. \qquad (12)$$

Replacing $S_{pore(r)}$ and $V_{pore(r)}$ with the surface area. $S_{imb(r)}$ and volume $V_{imb(r)}$ of imbibition pores in relationship (10) to further transform the relationship to calculate $K_{imb}$ into:

$$K_{imb} = \frac{\rho_2^2 \varphi S_w^3 V^2}{C\left(\sum\limits_{T_2=T_{2min}}^{T_{2max}} \frac{V_{imb(T_2)}}{T_2}\right)^2}; \qquad (13)$$

where $T_{2min}$ and $T_{2max}$ are the parameters corresponding to $r_{min}$ and rmax; $S_{imb(T2)}$ and $V_{imb(T2)}$ are the parameters corresponding to $S_{imb(r)}$ and $V_{imb(r)}$.

Relationship (13) is the relationship to calculate the imbibition permeability of porous media based on $T_2$ distribution obtained from imbibition experiment.

Capillary pressure is another important parameter affecting the velocity of imbibition. Considering the complexity of pore network in porous media, the average capillary pressure is needed for the derivation of the imbibition permeability. For a capillary with radius r, its capillary pressure is:

$$P(r) = \frac{2\sigma\cos\theta}{r}; \qquad (14)$$

where $\sigma$ is the surface tension between wetting and non-wetting phases (mN/m); cos $\theta$ is the cosine value of the contact angle.

Essentially, the average capillary pressure $P_{ave}$ is the weighted average value of capillary pressure for the pores with different sizes in porous medium, which can be obtained by:

$$R(r) = \frac{V_{pore(r)}}{Y}; \qquad (15)$$

where $V_{pore(r)}$ is the volume of pores with radius r in porous medium.

Therefore, the average pore pressure is the sum of the production of capillary pressure P(r) and its corresponding proportion R(r):

$$P_{ave} = \sum_{r=r_{min}}^{r_{max}} R(r)P(r) = \frac{2\sigma\cos\theta}{V} \sum_{r=r_{min}}^{r_{max}} \frac{V_{pore(r)}}{r}. \qquad (16)$$

Similar to relationship (13), the pore radius r can be substituted by $T_2$ in relationship (16):

$$P_{ave} = \frac{2\sigma\cos\theta}{F_s\rho_2 V} \sum_{T_2=T_{2min}}^{T_{2max}} \frac{V_{pore(T_2)}}{T_2}. \qquad (17)$$

Relationship (17) is the relationship to calculate the average pore pressure $P_{ave}$ based on $T_2$ distribution of saturated porous medium.

The relationship between $T_2$ value and volume of pores in rock core sample can be obtained using the $T_2$ distribution of the first sample, and then the average pore pressure can be obtained using relationship (17).

Step 400, inserting the imbibition permeability, the average pore pressure, and the surface relaxivity into a Handy relationship to substitute for corresponding parameters to obtain a mathematical model for the spontaneous imbibition process of porous media basing on NMR.

Inserting the imbibition permeability $K_{imb}$ and the average pore pressure $P_{ave}$ obtained by the steps above (Eqs. 13 and 17) into relationship (1):

$$M = \qquad (18)$$

$$A\sqrt{\frac{2K_{imb}\varphi S_w P_{ave}}{\mu}}t = \frac{2A\varphi S_w^2 V}{\sum\limits_{T_2=T_{2min}}^{T_{2max}} \frac{V_{imb(T2)}}{T_2}} \sqrt{\frac{\rho_2\sigma\cos\theta \sum\limits_{T_2=T_{2min}}^{T_{2max}} \frac{V_{pore(T_2)}}{T_2}}{CF_s V\mu}}t.$$

In this relationship, the pore shape factor Fs equals 2 and the Kozeny-Carman constant C equals 6 for cylindrical pores;

Relationship (18) is the imbibition model for the imbibition volume versus time in porous media based on NMR theory. The calculation of this model can either be conducted by inserting $K_{imb}$ and $P_{ave}$ into relationship (1) or directly use relationship (18). But it should be noticed that the parameter $V_{imb(T2)}$ in relationship (18) is different from $V_{pore(T2)}$, which represent the pore volume corresponding to $T_2$ value under saturation state during spontaneous imbibition and the pore volume corresponding to $T_2$ value of saturated fluid sample respectively.

The following is a brief description of the step for this embodiment:

Sample Pretreatment and Basic Analysis

The selection, preparation and cleaning of rock samples are conducted according to the national standard of GB/T 29172-2012 "Practices for core analysis". Two parallel core plug samples with 2.5 cm in diameter and 5 cm in height are drilled from the rock vertical to its bedding direction. They are cleaned and dried at 105° C. for 48 hours until mass remained unchanged to ensure there is no residual water in pores. Then, the mass of dry samples m0 is measured using a high precise electronic balance, and their helium porosity $\varphi$ and contact angle $\theta$ are then measured according to the national standard.

NMR Measurement Under Saturated State for Base Signal

In this experiment, the CPMG pulse sequence is applied in NMR measurements, and parameters for all NMR $T_2$ measurements are set as follows: echo spacing of 0.132 ms, echo numbers of 3788, scan number of 32, and recycle delay of 750 ms. These parameters are set as default in all NMR $T_2$ measurements in the present disclosure.

The calibration is conducted on the rock sample for their base signal before experiment. After preparation, two dry core plug samples are conducted on NMR experiment to Obtain the samples' $T_2$ distributions under dry state, which are considered to be the base signal in the following experiments. Then, the first sample is conducted on the fully-saturated and centrifuged experiments. First, put the first core sample into a vacuum pump and vacuum for 8 h, then inject 3% (about 30000 ppm) KCl solution into the pump and pressurize to 30 MPa (about 3000 psi). Maintain the pressure for 24 hours to ensure the core sample reaches fully-saturated state. The KCl solution used in this step can avoid the swelling of clay in core sample.

After the fully-saturated process, the first sample is taken out from pump and the excess liquid is wiped off from surface, then it is weighed and the mass is recorded as m1. After that, the NMR analysis is conducted to obtain the $T_2$ distribution of pores and the mass of water m(m=m$_1$−m$_0$) for the saturated sample.

Centrifugation and the Calculation of Surface Relaxivity

The saturated sample is then centrifuged under centrifugal pressure $P_c$, and the mass of sample before and after centrifugation is recorded. NMR $T_2$ measurements are also conducted during this process to obtain the $T_2$ distributions under fully-saturated and centrifuged states, and the sample's $T_{2c}$ is calculated using these data. Then, the centrifugal radius $r_c$ is calculated by substituting $P_c$ into relationship (2), and the surface relaxivity $\rho_2$ can be obtained using relationship (4).

The Calculation of the Mathematical Model for Spontaneous Imbibition

The imbibition permeability $K_{imb}$ can be obtained by substituting $T_2$ distributions of the first sample under fully-saturated and centrifuged states and $T_2$ distribution of the second sample under imbibition saturated state into relationship (13). Then, the average pore pressure can be obtained by substituting $T_2$ distribution of the first sample under fully-saturated state into relationship (17). Finally, the NMR-based mathematical model for spontaneous imbibition can be obtained by inserting $P_{ave}$ and $K_{imb}$ into relationship (18).

The present disclosure overcomes the limitations in the traditional Handy model that the permeability and capillary pressure is hard to obtain and lacks accuracy by traditional experimental methods. Besides, the present disclosure also provides a new approach to evaluate the influence of imbibition on hydraulic fracturing during the development of tight reservoirs like shales.

The present disclosure is able to predict the relationship of imbibition volume versus time and can be used for the analysis of the performance of hydraulic fracturing of tight reservoirs in petroleum engineering, and it also has broad application prospects to study physical properties in petrology and material science. Apart from tight reservoir rocks such as shales, it is also suitable for the study of other kinds of natural porous media such as sandstones, carbonate rocks and soil. Meanwhile, it also has application prospects to evaluate the physical property of some man-made materials.

The scheme of the present disclosure is further described below with specific embodiments.

In this embodiment, the spontaneous imbibition process of shale core plug samples was taken as an example, and distilled water (with $\rho = 1$ g/cm$^3$ and $\sigma = 72.75$ mN/m) was chosen as the working liquid. The experiment was conducted at ambient temperature (20° C.) and pressure (0.1 MPa). The helium porosity is of the rock sample was 4.52%.

Two paralleled core plug samples with 2.5 cm in diameter and 5 cm in height were drilled from the shale sample marked a1, a2. The masses of sample a1, a2 were 61.31 g and 61.88 g, and the contact angels of them were 41.11° and 44.74° respectively. The pores in shale is regarded as capillaries, and thus the pore shape factor Fs equals 2 and Kozeny-Carman constant C equals 6 in this experiment.

Sample a2 was selected to conduct the fully saturated and centrifugal experiments and sample a1 was selected to conduct the spontaneous imbibition experiment. FIG. 2 is the $T_2$ distributions of sample a2 under fully-saturated and centrifuged ($P_c = 2.74$ MPa) states. According to relationship (2), the centrifugal radius $r_c$ is:

$$r_c = \frac{2\sigma}{P_c} = \frac{2 \times 72.75 \text{ mN/m}}{2.74 \text{ MPa}} = 53.10 \text{ nm}$$

Figure 3:
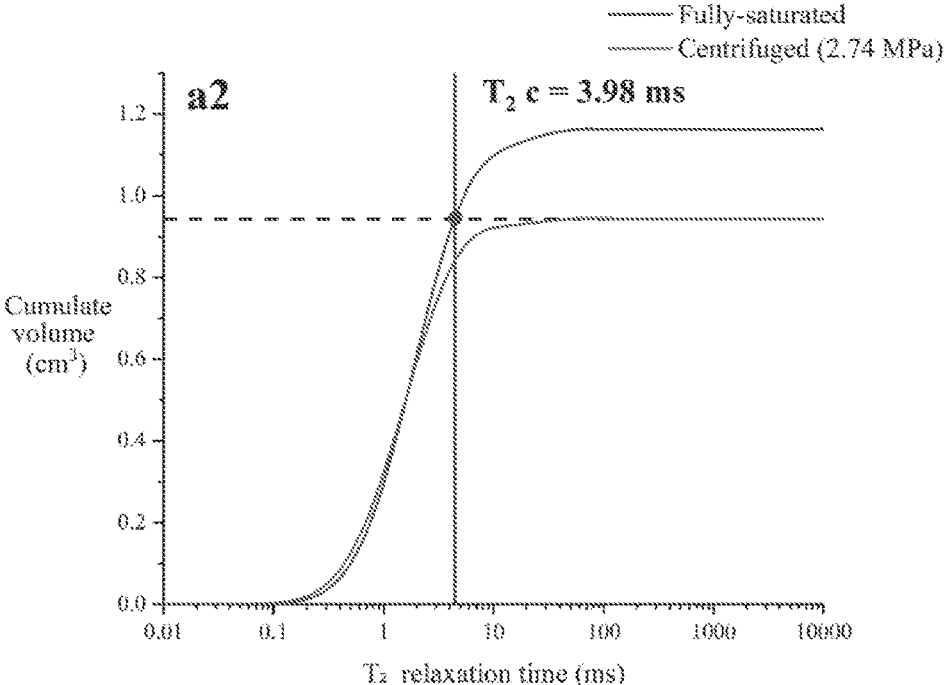
FIG. 3 is a schematic diagram of cumulative NMR $T_2$ distribution of sample a2 under saturated and centrifuged state according to one embodiment of the present disclosure.

The volume of water in a2 under fully-saturated state is 1.16 cm$^3$ (similar to the volume calculated by helium porosity), and after centrifugation there is still 0.89 cm$^3$ residual water in it. In FIG. 3, it can be seen that the cumulative volume of a2 when $T_2 = 3.98$ ms under fully-saturated state equals the total water volume under centrifuged state. Thus, $T_{2c}$ equals 3.98 ms and the surface relaxivity can be calculated using relationship (4):

$$\rho_2 = \frac{r_c}{F_s T_{2c}} = \frac{53.10 \text{ nm}}{2 \times 3.98 \text{ ms}} = 6.67 \text{ nm/ms}$$

The water volume of a2 (1.16 cm$^3$) under saturated state is its total pore volume V, and $P_{ave}$ can be obtained by inserting the data of fully-saturated $T_2$ distribution in FIG. 2 into relationship (17):

$$P_{ave} = \frac{2\sigma\cos\theta}{F_s \rho_2 V} \sum_{T_2 = T_{2min}}^{T_{2max}} \frac{V_{pore(T_2)}}{T_2} =$$

$$\frac{2 \times 72.75 \text{ mN/m} \times \cos 44.74°}{2 \times 6.67 \text{ nm/ms} \times 1.16 \text{ cm}^3} \times 0.93 \text{ cm}^3/\text{ms} = 6.19 \text{ MPa}$$

Figure 4:
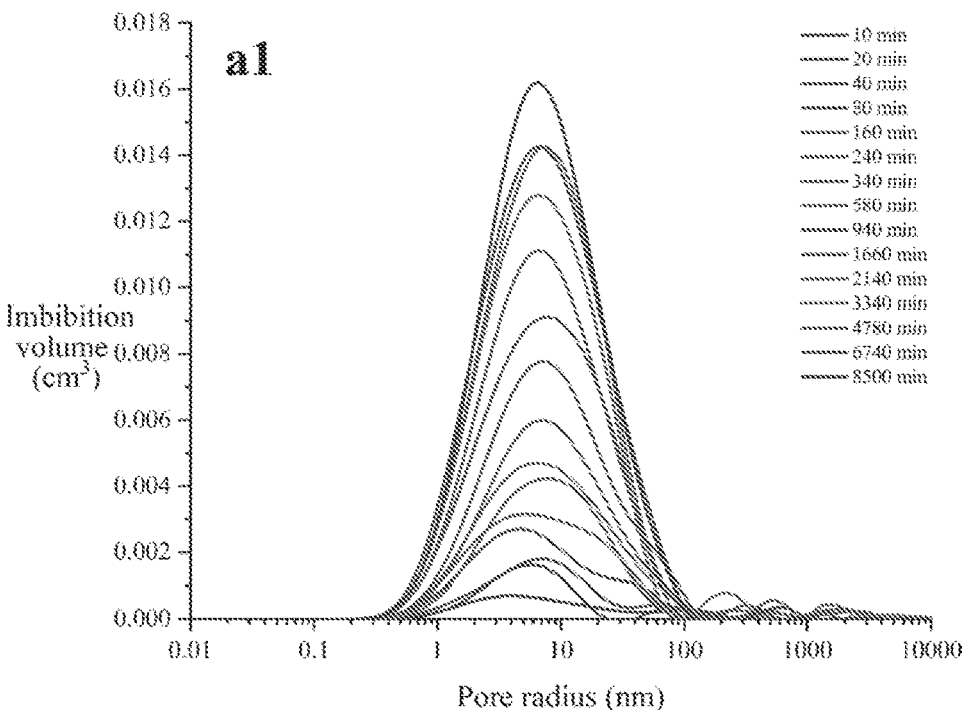
FIG. 4 is a schematic diagram of NMR $T_2$ distributions of a1 after spontaneous imbibition experiment according to one embodiment of the present disclosure.

FIG. 4 is the NMR $T_2$ distributions of a1 during imbibition process. It can be calculated that the maximum imbibition volume of a1 is 0.35 cm$^3$, and the corresponding saturation $S_w$ is 31.98% (take a2 as the standard). Based on the $T_2$ distribution of a1 under imbibition saturated state, the imbibition permeability $K_{imb}$ of a1 can be obtained by using relationship (13):

$$K_{imb} = \frac{\rho_2^2 \varphi S_w^3 V^2}{C\left(\sum_{T_2 = T_{2min}}^{T_{2max}} \frac{V_{imb(T_2)}}{T_2}\right)^2} =$$

$$\frac{(6.60 \text{ nm/ms})^2 \times 00452 \times (0.3198)^3 \times (1.10 \text{ cm}^3)^2}{6 \times (1.15 \text{ cm}^3/\text{ms})^2} = 1.18 \times 10^{-5} \text{mD}$$

As $K_{imb}$ and $P_{ave}$ are known, the mathematical model of imbibition volume versus time for the rock core samples can be obtained:

$$M = A\sqrt{\frac{2K_1 \varphi S_w P_{ave}}{\mu}t} =$$

$$4.91 \text{ cm}^2 \times \sqrt{\frac{2 \times 1.15 \times 10^{-5} \text{mD} \times 0.0452 \times 1.3198 \times 6.18 \text{ MPa}}{0.89 \times 10^{-3} \text{Pa} \cdot \text{s}}t} =$$

$$4.29 \times 10^{-2} \text{min}^{-0.5} \times \sqrt{t}$$

Figure 5:
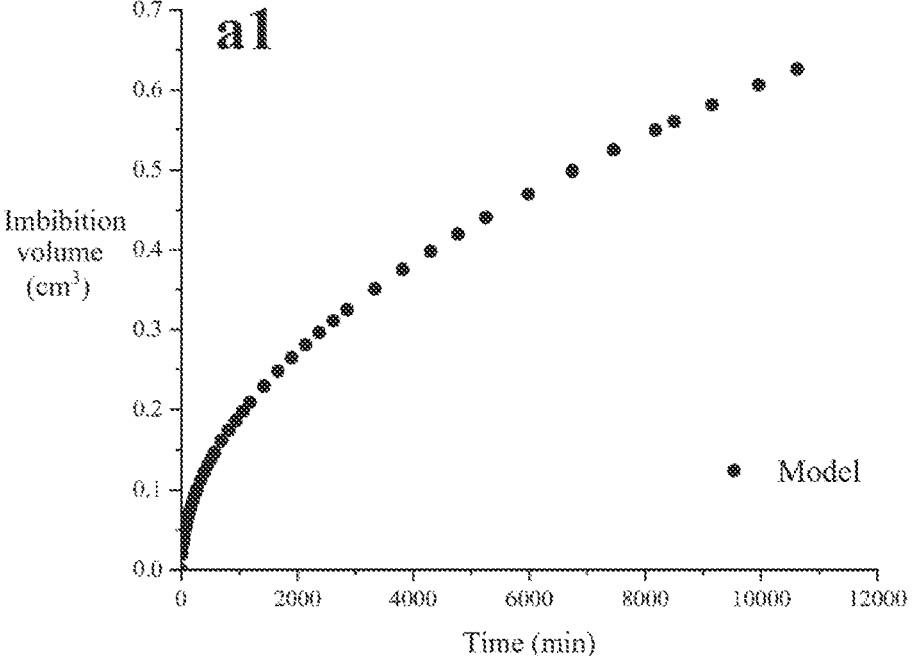
FIG. 5 is a schematic diagram of a relationship of imbibition volume and time of a1 simulated by the model according to one embodiment of the present disclosure.

The simulation of new spontaneous imbibition model for a1 is shown in FIG. 5.

So far, the researchers in this field should recognize that although a plurality of exemplary embodiments of the present disclosure have been shown and described in detail, many other variants or modifications in accordance with the principles of the present disclosure can be directly determined or derived from the contents of the present disclosure without departing from the spirit and scope.

What is claimed is:

1. A method for establishing mathematical model of relationship between spontaneous imbibition volume and time of porous medium in a spontaneous imbibition process, comprising following steps:

step 100, selecting two parallel rock core plug samples for pretreatment, cleaning and drying the two parallel rock core plug samples, evacuating a first rock core plug sample and then injecting the first rock core plug sample with water to obtain a fully-saturated sample; then centrifuging the first rock core plug sample and recording changes of weight and nuclear magnetic resonance (NMR) $T_2$ distributions to obtain water distribution characteristics of the fully-saturated sample in pores, wherein the selecting two parallel rock core plug samples for pretreatment, cleaning and drying the two parallel rock core plug samples comprising: drilling the two parallel core plug samples from the rock vertical to its bedding direction, cleaning and drying the two parallel core plug samples at 105° C. for 48 hours until mass remained unchanged, and the evacuating a first rock core plug sample and then injecting the first rock core plug sample with water to obtain a fully-saturated sample comprising: put the first rock core plug sample into a vacuum pump and vacuum for 8 hours, then injecting 3% KCl solution into the pump and pressurize to 30 MPa, and maintaining the pressure for 24 hours, and the centrifuging the first rock core plug sample and recording changes of weight and nuclear magnetic resonance (NMR) $T_2$ distributions comprising: centrifugating the fully-saturated sample under centrifugal pressure and recording a mass of the sample before and after centrifugation;

step 200, conducting spontaneous imbibition experiment on a second rock core plug sample, conducting NMR analysis on a result of the spontaneous imbibition experiment to obtain a $T_2$ distribution of the second rock core plug sample;

step 300, plotting cumulative volume distributions of the first rock core plug sample under fully-saturated and imbibition saturated states, to obtain a $T_2$ value ($T_{2c}$) when a cumulative volume in fully-saturated distribution equals to a total volume of a centrifuged sample and to obtain a centrifugal radius and surface relaxivity through $T_{2c}$ then calculating imbibition permeability and average pore pressure through porosity of the first rock core plug, saturation, and the $T_2$ distribution of the second rock core plug sample under the fully-saturated state; and step 400, obtaining a mathematical model for the spontaneous imbibition process of porous media based on NMR by using the imbibition permeability, the average pore pressure, and the surface relaxivity based on a classical Handy relationship to substitute for corresponding parameters therewith.

2. The method for establishing mathematical model of relationship between spontaneous imbibition volume and time of porous medium in a spontaneous imbibition process according to claim 1, wherein in step 300, a relationship to calculate an imbibition permeability $K_{imb}$ of the porous medium based on an imbibition saturated $T_2$ distribution data is as following:

$$K_{imb} = \frac{\rho_2^2 \varphi S_w^3 V^2}{C\left(\sum_{T_2=T_{2min}}^{T_{2max}} \frac{V_{imb(T_2)}}{T_2}\right)^2};$$ (13)

where a unit of $K_{imb}$ is $10^{-3}$md; $\rho_2$ is the surface relaxivity, the $\rho_2$ is only related to a type of the porous medium and has a unit of nm/ms; $\varphi$ is total porosity and is dimensionless; Sw is the water saturation and is dimensionless; V is the total pore volume, $cm^3$; C is a Kozeny-Carman constant and is dimensionless; $T_2$ is transverse relaxation time, ms; $T_{2max}$ is the $T_2$ value corresponding to a maximum pore radius in $T_2$ distribution spectra, ms; $T_{2min}$ is the $T_2$ value corresponding to a minimum pore radius in $T_2$ distribution spectra, ms; $V_{imb(T2)}$ is the volume of imbibition pores with relaxation time $T_2$, $cm^3$.

3. The method for establishing mathematical model of relationship between spontaneous imbibition volume and time of porous medium in a spontaneous imbibition process according to claim 2, wherein a calculation process of the imbibition permeability $K_{imb}$ is as following:

predicting a semi empirical relationship frequently configured to study permeability of the porous medium according to the Kozeny-Carman relationship:

$$K = \frac{\varphi^3}{C\gamma^2},$$ (5)

where $\varphi$ is the total porosity, C is Kozeny-Carman constant; $\gamma$ is a ratio of a total surface area of pores to the sample volume ($m^{-1}$);

if the porosity, volume, and surface area of pores participating in imbibition in the porous medium (called imbibition pores) are respectively denoted as $\varphi_{imb}$, $V_{imb}$, and $S_{imb}$, the $V_{imb}$ and $\varphi_{imb}$ have a following relationship with the total porosity $\varphi$ and saturation $S_w$:

$$\varphi_{imb} = \frac{V_{imb}}{V_{sample}} = \frac{VS_W}{V_{sample}} = \varphi S_W;$$ (7)

where V is a volume of all pores in porous medium ($cm^3$);

obtaining the imbibition permeability $K_{imb}$ for the imbibition process by inserting $\varphi_{imb}$, $V_{imb}$, and $S_{imb}$ into the Kozeny-Carman relationship:

$$K_{imb} = \frac{\varphi_{imb}^3}{C\gamma^2} = \frac{\varphi_{imb}^3 V_{sample}^2}{CS_{imb}^2} = \frac{\varphi^3 S_w^3 V_{sample}^2}{CS_{imb}^2};$$ (8)

as a surface area $S_{imb}$ of imbibition pores is a sum of the surface area of pores participating in imbibition process, and a volume of sample $V_{sample}$ equals to a ratio of total pore volume and porosity, thereby satisfying following relationships:

$$S_{imb} = \sum_{r=r_{min}}^{r_{max}} S_{imb(r)}; \text{ and}$$ (9)

$$V_{sample} = \frac{V}{\varphi};$$ (10)

and simplifying the calculation of imbibition permeability $K_{imb}$ as a following relationship:

$$K_{imb} = \frac{\varphi S_w^3 V^2}{C\left(\sum_{r=r_{min}}^{r_{max}} S_{imb(r)}\right)^2};$$ (11)

where $r_{max}$ is a maximum pore radius and $r_{min}$ is a minimum pore radius in porous medium and $S_{imb(r)}$ is the pore surface area of the imbibition pores with radius r;

the $T_2$ signal in fully-saturated pores of porous medium are mainly contributed by a surface relaxation $T_{2s}$, thereby satisfying a following relationship:

$$\frac{t}{T_2} \approx \frac{1}{T_{2S}} = \rho_2 \left( \frac{S_{pore(r)}}{V_{pore(r)}} \right); \tag{3}$$

where $\rho_2$ is the surface relaxivity (nm/ms) and is constant; $S_{pore(r)}$ and $V_{pore(r)}$ are the surface area and volume of pores with radius r in porous medium;

a following relationship is further satisfied:

$$S_{pore(r)} = \frac{V_{pore(r)}}{\rho_2 T_2}; \tag{12}$$

respectively substituting $S_{pore(r)}$ and $V_{pore(r)}$ with $S_{imb(r)}$ and $V_{imb(r)}$, and inserting these parameters into a following relationship to calculate the imbibition permeability $K_{imb}$;

$$K_{imb} = \frac{\rho_2^2 \varphi S_w^3 V^2}{c \left( \sum_{T_2 = T_{2min}}^{T_{2max}} \frac{V_{imb(T_2)}}{T_2} \right)^2}; \tag{13}$$

where $S_{imb(T2)}$ and $V_{imb(T2)}$ are the surface area and volume of pores corresponding to transverse relaxation time $T_2$ (further equivalent to $S_{imb(r)}$, $V_{imb(r)}$).

4. The method for establishing mathematical model of relationship between spontaneous imbibition volume and time of porous medium in a spontaneous imbibition process according to claim 3, wherein a calculation process of the surface relaxivity $\rho_2$ mentioned in the calculation of the imbibition permeability $K_{imb}$ is as following:

satisfying a relationship between centrifugal pressure $P_c$ and centrifugal radius $r_c$ as following:

$$r_c = \frac{2\sigma}{P_c}; \tag{2}$$

wherein $\sigma$ is the surface relaxivity (mN/m); regarding $T_2$ value corresponding to radius r as the $T_2$ (or $T_{2c}$) corresponding to the centrifugal radius $r_c$ for the sample; inserting $r_c$ and $T_{2c}$ into the relationship (3) to obtain a following relationship to calculate the surface relaxivity $\rho_2$:

$$\rho_2 = \frac{r_c}{F_s T_{2c}}; \tag{4}$$

where Fs is a pore shape factor.

5. The method for establishing mathematical model of relationship between spontaneous imbibition volume and time of porous medium in a spontaneous imbibition process according to claim 4, wherein a process to calculate the centrifugal radius $r_c$ under centrifugal pressure $P_c$ using the pore radius obtained by $T_2$ value is as following:

if the pores larger than centrifugal radius in rock core sample can be completely discharged after centrifugation, obtaining the centrifugal radius through the cumulative $T_2$ distributions of the sample, because if the total $T_2$ signal under centrifuged state equals the cumulative $T_2$ signal when the transverse relaxation time equals $T_2$, regarding transverse relaxation time value as the $T_2$ value corresponding to the centrifuged radius $r_c$.

6. The method for establishing mathematical model of relationship between spontaneous imbibition volume and time of porous medium in a spontaneous imbibition process according to claim 1, a calculation process of $P_{ave}$ in step 300 is as following:

regarding the pores as capillaries in the porous medium, a capillary pressure P(r) for pores with radius r satisfies a following relationship:

$$P(r) = \frac{2\sigma \cos\theta}{r}; \tag{14}$$

where $\sigma$ is the surface relaxivity (mN/m); cos $\theta$ is a cosine value of a contact angle;

calculating the weight of pores with different sizes through a following relationship:

$$R(r) = \frac{V_{pore(r)}}{V}; \tag{15}$$

were $V_{pore(r)}$ is the volume of pores with radius r;

calculating an average pore pressure $P_{ave}$ through a following relationship where the average pore pressure $P_{ave}$ is a sum of a production of capillary pressure P(r) and its corresponding proportion R(r):

$$P_{ave} = \sum_{r=r_{min}}^{r_{max}} R(r)P(r) = \frac{2\sigma \cos\theta}{V} \sum_{r=r_{min}}^{r_{max}} \frac{V_{pore(r)}}{r}; \tag{16}$$

wherein V is the total pore volume, cm³; $r_{max}$ is a maximum pore radius and $r_{min}$ is a minimum pore radius in porous medium; substituting the pore radius r by $T_2$ to obtain the relationship to calculate the average capillary pressure $P_{ave}$ through a following relationship:

$$P_{ave} = \frac{2\sigma \cos\theta}{F_s \rho_2 V} \sum_{T_2 = T_{2min}}^{T_{2max}} \frac{V_{pore(T_2)}}{T_2}; \tag{17}$$

wherein $T_2$ is transverse relaxation time, ms; $T_{2max}$ is the $T_2$ value corresponding to a maximum pore radius in $T_2$ distribution spectra, ms; $T_{2min}$ is the $T_2$ value corresponding to a minimum pore radius in $T_2$ distribution spectra, ms; $\rho_2$ is the surface relaxivity (nm/ms) and is constant; Fs is a pore shape factor, analyzing the relationship between $T_2$ value and its corresponding pore volume through the $T_2$ distribution of the porous medium under fully-saturated state, and calculating the average pore radius based on the average pore radius.

7. The method for establishing mathematical model of relationship between spontaneous imbibition volume and time of porous medium in a spontaneous imbibition process according to claim 1, wherein the mathematical model in step 400 is as follows:

$$M = \frac{2A\varphi S_w^2 V}{\sum_{T_2=T_{2min}}^{T_{2max}} \frac{V_{imb(T_2)}}{T_2}} \sqrt{\frac{\rho_2\sigma\cos\theta \sum_{T_2=T_{2min}}^{T_{2max}} \frac{V_{pore(T_2)}}{T_2}}{CF_s V\mu}t}; \quad (18)$$

where A is a contact area between sample and fluid, cm$^2$; μ is a viscosity of fluid, Pa·s; t is time, s; for cylindrical pores, a pore shape factor Fs equals 2 and a Kozeny-Carman constant C equals 6; $V_{imb(T2)}$ and $V_{pore(T2)}$ respectively represents the pore volume of the pores with transverse relaxation time equals $T_2$ under imbibition saturated state and fully-saturated state; $\rho_2$ is the surface relaxivity, the $\rho_2$ is only related to a type of the porous medium and has a unit of nm/ms; φ is total porosity and is dimensionless; Sw is the water saturation and is dimensionless; V is the total pore volume, cm$^3$; C is the Kozeny-Carman constant and is dimensionless; $T_2$ is transverse relaxation time, ms; $T_{2max}$ is the $T_2$ value corresponding to a maximum pore radius in $T_2$ distribution spectra, ms; $T_{2min}$ is the $T_2$ value corresponding to a minimum pore radius in $T_2$ distribution spectra, ms; cos θ is a cosine value of a contact angle; σ is the surface relaxivity (mN/m);

the mathematical model is obtained by inserting $K_{imb}$ and $P_{ave}$ into the classical Handy relationship or the relationship (18) is directly used as the mathematical model.

*   *   *   *   *